US012308095B1

(12) United States Patent
Olson et al.

(10) Patent No.: US 12,308,095 B1
(45) Date of Patent: May 20, 2025

(54) PREDICTION OF COMPUTATIONAL PATHWAY CIRCUITS

(71) Applicant: NantBio, Inc., Culver City, CA (US)

(72) Inventors: Clifford Anders Olson, Long Beach, CA (US); Kayvan Niazi, Agoura Hills, CA (US); Nicholas J. Witchey, Laguna Hills, CA (US); Wael Tadros, Los Angeles, CA (US)

(73) Assignee: NantBio, Inc., Culver City, CA (US)

( * ) Notice: Subject to any disclaimer, the term of this patent is extended or adjusted under 35 U.S.C. 154(b) by 399 days.

(21) Appl. No.: 16/891,935

(22) Filed: Jun. 3, 2020

Related U.S. Application Data

(60) Provisional application No. 62/860,142, filed on Jun. 11, 2019.

(51) Int. Cl.
G16B 5/00 (2019.01)
G16B 25/10 (2019.01)

(52) U.S. Cl.
CPC .............. G16B 5/00 (2019.02); G16B 25/10 (2019.02)

(58) Field of Classification Search
CPC ...... G01N 33/5023; G16B 5/00; G16B 25/10; C12N 15/85
See application file for complete search history.

(56) References Cited

U.S. PATENT DOCUMENTS

| 4,997,913 | A | 3/1991 | Hellstrom et al. | |
|---|---|---|---|---|
| 7,396,910 | B2 | 7/2008 | Bevan et al. | |
| 2003/0003519 | A1* | 1/2003 | Khodadoust | C12N 15/85 435/7.21 |
| 2003/0138419 | A1 | 7/2003 | Radic et al. | |
| 2008/0267978 | A1 | 10/2008 | Zutter | |
| 2011/0027186 | A1 | 2/2011 | Hong et al. | |
| 2011/0191912 | A1* | 8/2011 | Alexandrov | C07K 14/415 435/468 |
| 2011/0312001 | A1* | 12/2011 | Nuwaysir | G01N 33/5023 435/8 |
| 2012/0015839 | A1 | 1/2012 | Chinnaiyan | |
| 2012/0041683 | A1 | 2/2012 | Vaske et al. | |
| 2012/0084885 | A1* | 4/2012 | Alexandrov | C12N 15/8216 435/468 |
| 2012/0158391 | A1 | 6/2012 | Vaske et al. | |
| 2012/0159672 | A1* | 6/2012 | Alexandrov | C07K 14/415 536/23.6 |
| 2017/0183654 | A1 | 6/2017 | Wong et al. | |
| 2019/0336516 | A1* | 11/2019 | Soon-Shiong | C07K 16/244 |

FOREIGN PATENT DOCUMENTS

| JP | 2006508643 | A | * | 3/2006 | | |
|---|---|---|---|---|---|---|
| WO | 03/047526 | A3 | | 11/2003 | | |
| WO | 2006/008484 | A3 | | 9/2006 | | |
| WO | 2006/110091 | A1 | | 10/2006 | | |
| WO | WO-2009039300 | A2 | * | 3/2009 | ......... | C12N 15/113 |
| WO | 2010/021822 | A3 | | 6/2010 | | |
| WO | WO-2013062505 | A1 | * | 5/2013 | ......... | G06F 16/2219 |
| WO | 2015/069770 | A1 | | 5/2015 | | |
| WO | 2017/066256 | A4 | | 7/2017 | | |
| WO | 2017/205810 | A8 | | 1/2018 | | |
| WO | 2018/089637 | A4 | | 7/2018 | | |

OTHER PUBLICATIONS

Angela, Process and materials for production of glucosamine and N-acetyl glucosamine, 2006, Japan Platform for Patent Information, pp. 1-298 (Year: 2006).*
Daringer et al., Modular Extracellular Sensor Architecture for Engineering Mammalian Cell-based Devices, 2014, ACS Publications, pp. 892-902 (Year: 2014).*
Weinberg et al., "Large-scale design of robust genetic circuits with multiple inputs and outputs for mammalian cells", nature biotechnology, 2017, vol. 35, No. 5, 12 pages (Cited from Specification).
Sharif et al., "Cell density regulates cancer metastasis via the Hippo pathway", Future Oncol., 2015, vol. 11, No. 24, pp. 3253-3260 (Cited from Specification).
Christopher et al., "The Structural and Functional Basis of Cytokine Receptor Activation: Lessons From the Common b Subunit of the Granulocyte Macrophage Colony-Stimulating Factor, Interleukin-3 (IL-3), and IL-5 Receptors", Blood, Mar. 1, 1997, vol. 89, No. 5, pp. 1471-1482 (Cited from Specification).
Palomino et al., "Chemokines and immunity", einstein, 2015, vol. 13, No. 3, pp. 469-473 (Cited from Specification).
Damaghi et al., "pH sensing and regulation in cancer", frontiers in Physiology, 2013, vol. 4, No. 370, pp. 1-10 (Cited from Specification).
Blad et al., "G protein-coupled receptors for energy metabolites as new therapeutic targets", Nature Reviews Drug Discovery, 2012, vol. 11, 603-619 (Cited from Specification).
Yuan et al., "Nutrient sensing, metabolism, and cell growth control", Mol Cell. Feb. 7, 2013, vol. 49, No. 3, 16 pages (Cited from Specification).
Tkach et al., "Communication by Extracellular Vesicles: Where We are and Where We Need to Go", Cell, Mar. 1, 20160, vol. 165, pp. 1226-1232 (Cited from Specification).
Ghazarian et al., "A glycobiology review: carbohydrates, lectins, and implications in cancer therapeutics" Acta Histochem, May 2011, vol. 113, No. 3, 26 pages (Cited from Specification).
Nishida Naoyo et al., "Angiogenesis in cancer", Vascular Health and Risk Management, 2006, vol. 2, No. 3, pp. 213-219 (Cited from Specification).

(Continued)

Primary Examiner — Ryan F Pitaro
Assistant Examiner — Bernard E Cothran
(74) Attorney, Agent, or Firm — Umberg Zipser LLP

(57) ABSTRACT

Described herein are methods of making recombinant cells using an in silico-generated pathway map of an endogenous pathway in a cell of interest to determine, in silico, a predicted effect of incorporating a recombinant nucleic acid into the endogenous pathway; and based on the predicted effect, incorporating the recombinant nucleic acid into the endogenous pathway in the cell of interest such that activation of the endogenous pathway regulates expression of the recombinant nucleic acid.

8 Claims, No Drawings

(56) References Cited

OTHER PUBLICATIONS

Ward et al., "Biomarkers of apoptosis" British Journal of Cancer, 2008, vol. 99, pp. 841-846 (Cited from Specification).
Akira et al., "Pathogen Recognition and Innate Immunity", Cell, 2006, vol. 124, pp. 783-801 (Cited from Specification).
Zhu et al., "How Do Cells Sense Oxygen?", Science, Apr. 20, 2001, vol. 292, No. 5516, 3 pages (Cited from Specification).
Moqrich et al., "Impaired Thermosensation in Mice Lacking TRPV3, a Heat and Camphor Sensor in the Skin", Science, 2005, vol. 307, pp. 1468-1472 (Cited from Specification).

\* cited by examiner

PREDICTION OF COMPUTATIONAL PATHWAY CIRCUITS

This application claims priority to U.S. provisional patent application with the Ser. No. 62/860,142, which was filed Jun. 11, 2019, which is incorporated by reference herein in its entirety.

FIELD OF THE INVENTION

The field of the inventions is technologies related to empirically validating computationally derived proteomic pathway influences.

BACKGROUND

The background description includes information that may be useful in understanding the present invention. It is not an admission that any of the information provided herein is prior art or relevant to the presently claimed invention, or that any publication specifically or implicitly referenced is prior art.

The development of personalized immunotherapies continues to grow and appears to have a positive impact on the patient's prognosis. One aspect of the development of personalized immunotherapies is to determine if a patient would be responsive or non-responsive to a given treatment including drugs. For example, some effort has been directed to in silico analysis of proteomic pathways to determine influence of drugs with respect to expressed or non-expressed proteins as described in US patent published applications US20120041683 and US2012015839. The technology described in these patent applications is called PARADIGM.

PARADIGM, as well as other computation pathway analysis systems, incorporate known or otherwise measured elements of proteomic pathways (e.g., DNA sequences, RNA sequences, activities, etc.) along with unknown elements to form pathway models. The pathway models are then used make predictions of pathway behavior based on proposed therapies.

Proposed therapies or treatments can include one or more recombinant cell therapies (e.g., NK cells, T-Cells, etc.) where the recombinant cells have been heavily modified to express desirable therapeutic features. One type of recombinant cell therapy could include using cells that leverage "compunomics" where the cell's genomic structure has been modified to conditionally express (or not express) proteins based on the cell's surrounding micro environment. Cells created based on compunomics exhibit, more or less, computational features based on their genomic structure. Examples of such cells are described in co-owned applications 62/730,981 titled "Conditional Living Sensors", filed Sep. 13, 2018; 62/821,117 titled "Therapy Production Cellular Reporting", filed Mar. 20, 2019; and 62/819,113 titled "Conditional Modulation of Therapy using Recombinant Cells", filed Mar. 15, 2019. These cells are constructed to report information based on conditions of their environments. Unfortunately, modifications of the cells to exhibit computational features can impact one or more other pathways of the cell as mentioned above in an undesirable or possibly unforeseen manner.

SUMMARY OF THE INVENTION

The inventors have appreciated that it would be beneficial to determine a priori if "computational" modifications to modified cells would have the desired impact according to design. For example, it would be useful to determine if the newly introduced compunomic features would not interfere in desirable proteomic pathways or would interfere in a desirable proteomic pathway according to design. In another example, it would be useful to use pathway knowledge of an existing cell to impart new pathway-based traits that are otherwise not native to the modified cell. More specifically, there is a need for technologies (e.g., in silico, methods, etc.) that can identify pathways that would be available, or unavailable, for use in compunomic uses or therapies.

In an aspect of the inventive subject matter, provided herein are methods for making a recombinant cell. The methods include obtaining, in silico, a pathway map of an endogenous pathway in a cell of interest, determining, in silico, a predicted effect of incorporating a recombinant nucleic acid into the endogenous pathway; and based on the predicted effect, incorporating the recombinant nucleic acid into the endogenous pathway in the cell of interest such that activation of the endogenous pathway regulates expression of the recombinant nucleic acid, thereby making a recombinant cell.

In an aspect, provided herein are methods for making a recombinant cell. The methods include obtaining a pathway map of a first endogenous pathway and a second endogenous pathway in a cell of interest, determining a predicted first degree of impact on the first endogenous pathway of incorporating a first recombinant nucleic acid into the first endogenous pathway, and determining a predicted second degree of impact on the second endogenous pathway of incorporating a second recombinant nucleic acid into the second endogenous pathway. The methods include incorporating the first recombinant nucleic acid into the first endogenous pathway in the cell of interest, if the first degree of impact is of a first desired magnitude (e.g., none, low, medium, high, etc.), such that activation of the first endogenous pathway regulates expression of the first recombinant nucleic acid; and/or if the second degree of impact is of a second desired magnitude, incorporating the second recombinant nucleic acid into the second endogenous pathway in the cell of interest such that activation of the second endogenous pathway regulates expression of the second recombinant nucleic acid, thereby making a recombinant cell.

In an aspect, provided herein are systems including at least one data processor; and at least one memory storing instructions, which when executed by the at least one data processor, result in operations. The operations include creating a hybrid pathway model by at least connecting an endogenous pathway model for a cell coupled to an exogenous pathway model of the cell, the endogenous pathway model having at least one modeled activity, the exogenous pathway model comprising at least one factor for coupling the endogenous pathway model, and the endogenous pathway model and the exogenous pathway model being connected based on the at least one factor; and calculating, based at least on the hybrid pathway model, an activity in the exogenous pathway.

In an aspect, provided herein are methods including creating, by at least one data processor, a hybrid pathway model by at least connecting an endogenous pathway model with an exogenous pathway model, the endogenous pathway model having at least one modeled activity, the exogenous pathway model comprising at least one factor for coupling the endogenous pathway model, and the endogenous pathway model and the exogenous pathway model being connected based on the at least one factor; and calculating, based at least on the hybrid pathway model, a hybrid pathway activity.

In an aspect, provided herein are non-transitory computer readable medium storing instructions, which when executed by at least one data processor, result in operations. The operations include creating a hybrid pathway model by at least connecting an endogenous pathway model with an exogenous pathway model, the endogenous pathway model having at least one modeled activity, the exogenous pathway model comprising at least one factor for coupling the endogenous pathway model, and the endogenous pathway model and the exogenous pathway model being connected based on the at least one factor; and calculating, based at least on the hybrid pathway model, a hybrid pathway activity.

DETAILED DESCRIPTION

After reading this description, it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present technology is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "recombinant cell" refers to a cell that contains recombinant DNA or other genomic molecules (e.g., mtDNA, mRNA, tRNA, RNA, plasmids, etc.), which are molecules formed by laboratory methods of genetic recombination (such as molecular cloning) to bring together genetic material from multiple sources, creating sequences that would not otherwise be found in the native genome. The DNA sequences used in the construction of recombinant DNA molecules can originate from any species. For example, plant DNA may be joined to bacterial DNA, or human DNA may be joined with fungal DNA. In addition, DNA sequences that do not occur anywhere in nature may be created by the chemical synthesis of DNA, and incorporated into recombinant molecules. Using recombinant DNA technology and synthetic DNA, literally any DNA sequence may be created and introduced into any of a very wide range of living organisms. The term also encompasses cells in which mutations, insertions, deletions in a nucleic acid of the cell results in the desired change.

As used herein, the term "recombinant" is a species of the broader term "genetically modified" and is meant to encompass mutations, insertions, deletions that result in the desired change. "Genetic modification" is the process of altering the genetic makeup of an organism. This can be done by controlled, or selective, breeding of plants and animals, but as used herein refers to targeting a specific gene for more-precise alteration of the organism through genetic engineering.

As used herein, the term "in silico" refers to analysis or experimentation performed on computer or via computer simulation in reference to biological experiments.

As used herein, the term "endogenous pathway" refers to a naturally occurring set of processes, molecular events, and/or production systems that are utilized in a specific cell (e.g., fibroblast, lymphocyte, hepatocyte, etc.). It may be considered any process, molecular event, and/or production system native to the specific cell.

As used herein, the term "exogenous pathway" refers to a set of processes, molecular events, and/or production systems that are not normally utilized in a specific cell but have been genetically or molecularly engineered to be expressed and/or utilized in the specific cell. It may be considered any process, molecular event, and/or production system not native to the cell but recombinantly engineered into the specific cell.

As used herein, the term "pathway map" refers to the summary, a programmatic data structure, or graphical depiction of a linked series of reactions occurring within a cell that an be modeled on one or more computing devices. Each pathway may include a series of reactions that are connected by their intermediates: the products of one reaction are the substrates for subsequent reactions, and so on. For example, one pathway may be responsible for the synthesis of a particular amino acid, but the breakdown of that amino acid may occur via a separate and distinct pathway. In another example, a pathway may include a signaling pathway.

Non-limiting examples of pathways include regulatory pathway, signaling pathway, metabolic pathway, anabolic pathway, synthesis pathway, and the like. A pathway map can be generated via PARADIGM techniques as described in US2012/0041683 and US2012/015839, each of which is incorporated herein in its entirety. In more interesting embodiments, a pathway map can represent dozens, hundreds, or thousands or more interconnected pathways. For example, PARADIGM can support thousands of interconnected factor graphs forming a large scale pathway model.

As used herein, the term "degree of impact" refers to a stage in a scale of relative amount or intensity.

As used herein, the term "hybrid pathway" refers to a linked series of reactions occurring within a cell, some of which are native to the cell and others which may be recombinant and/or non-native. For example, a hybrid pathway may include one or more each of endogenous and exogenous pathways, one or more endogenous and exogenous pathway elements, and/or one or more each of endogenous and exogenous reactions.

As used herein, the term "data processor" refers to a computer or machine that carries out operations on data to retrieve, transform, or classify information.

As used herein, the term "memory storing instructions" refers to a particular set of computer engineering operands. Operands for all arithmetic and logic operations are contained in registers. To operate on data in main memory, the data is first copies into registers. A load operation copies data from main memory into register. A store operation copies data from a register into main memory.

As used herein, the term "operations" refers to a set of processes or events deriving one entity from others according to a rule.

The methods and systems described herein can be used to determine which pathway(s) in a particular cell can be utilized in order to make an engineered cell, for example, a recombinant cell that expresses one or more desired molecules (e.g., protein or RNA) under a particular set of conditions. By way of example only, and without limitation, a recombinant therapeutic cell can be made that expresses a therapeutic molecule. For example, the expression of the therapeutic molecule can be controlled when the cell is present in a particular microenvironment. For example, the microenvironment could be a tumor microenvironment where that microenvironment is characterized by one or more tumor-specific criteria (e.g., the presence of an associated molecule), one or more of which criteria can signal or otherwise cause the recombinant therapeutic cell to express the therapeutic molecule. Various microenvironment criteria that can be sensed by an engineered cell, as well as associated proteins and pathways that can be evaluated in silico, are provided in Table 1. For example, a cell can be engineered to sense one or more of the criteria listed in Table 1, such that the cell expresses at least one sensor protein that senses a molecule associated with the criteria when present in the cellular microenvironment. In response to the presence of the molecule, the engineered cell modulates the expression of another molecule, for example a therapeutic protein or a reporter protein. Engineered cells that can be made based on the information derived from the methods and systems described herein include, for example and without limitation, those described in U.S. Provisional Patent App. Nos. 62/821,117, filed Mar. 20, 2019; 62/819,113, filed Mar. 15, 2019; and 62/730,981, filed Sep. 13, 2018, each of which is incorporated in its entirety for all of its disclosure, including without limitation, all criteria, materials, compounds, compositions, molecules, proteins, components, methods of use and making.

TABLE 1

Microenvironment Criteria

| Criterion | Associated Molecule(s) | Sensor Protein(s) | References* |
|---|---|---|---|
| cell density | other cells in proximity | Hippo pathway, YAP, TAZ, GPCRs, e-cadherin | Sharif et al., Future Oncol. 2015 Dec.; 11(24): 3253-3260; US20110027186; WO2003047526 |
| cytokines | cytokine (e.g., chemokines, interferons, interleukins, lymphokines, and tumor necrosis factors) | cytokine receptors | Bagley et al., Blood 1997 89: 1471-1482, WO2006110091. |
| chemokines | chemokines (e.g., CXC, CX3C, CC, or C chemokines) | chemokine receptors (e.g., CXC chemokine receptors, CC chemokine receptors, CX3C chemokine receptors and XC chemokine receptors) | Palomino and Marti, Einstein (Sao Paulo) 2015 Jul.-Sep.; 13(3): 469-473. |
| pH | proton (H+) | acid-sensing ion channels (ASICs) and proton-sensing GPCRs (e.g., GPR4, GPR132, TDAG8, and OGR1); pH-sensitive conjugates | Damaghi et al., Front. Physiol. 2013 Vol. 4, Article 370; U.S. Pat. 4,997,913. |
| metabolites | metabolite (e.g., alcohol, amino acids, nucleotides, antioxidants, organic acids, polyols, vitamins, fatty acids, saccharides, lactate, ketone) | receptors (e.g., GPCRs) | Blad et al., Nature Reviews Drug Discovery volume 11, pages 603-619 (2012); Yuan et al., Mol Cell. 2013 Feb. 7; 49(3): 379-387. |

TABLE 1-continued

Microenvironment Criteria

| Criterion | Associated Molecule(s) | Sensor Protein(s) | References* |
| --- | --- | --- | --- |
| exosomes and other extracellular vesicles | exosomes, microvesicles, ectosomes, microparticles, surface molecules | receptors | Tkach and Thery, Cell 164, Mar. 10, 2016, 1226-1232. |
| sugars | sugar or sugar moiety | lectins, sucrose transporters, glucosensors | Ghazarian, et al., Acta Histochem. 2011 May; 113(3): 236-247. |
| Soluble immune checkpoint markers | PD-L1, PD-L2 | PD1, CTLA4 | Manson et al., Annals of Oncology, Volume 27, Issue 7, 1, Jul. 2016, Pages 1199-1206; WO2015069770. |
| angiogenic factors | VEGF, bFGF, TGF-α, TGF-β, platelet-derived endothelial growth factor, granulocyte colony-stimulating factor, placental growth factor, interleukin-8, hepatocyte growth factor, epidermal growth factor | receptors for each factor (e.g., VEGFR, TGFR, EGFR, IL receptors, etc.) | Nishida et al., Vasc Health Risk Manag. 2006 Sep.; 2(3): 213-219; US20080267978. |
| tumor-specific factors | neoepitopes; tumor-associated antigens | antibodies, CARs | WO2017205810; WO2017066256; WO2018089637 |
| apoptosis | apoptosis-associated factors (e.g., cleaved cytokeratin-18 (c-CK18), cleaved caspase-3 (c-cas-3), cleaved lamin A (c-lam-A), phosphorylated histone H2AX (gammaH2AX), cleaved poly(ADP ribose) polymerase (c-PARP), phosphatidylserine, Cytokeratins, Nucleosomal DNA, Apo-1/Fas, Fas ligand (sFasL), Bcl-2/Bcl-xl/Mcl-1, p53, phospo-p53, p21wafi, pH2AX, cytochrome c, Activated caspases 2, 3, 7, 8 and 9, fortilin) | receptors, antibodies | Ward et al., British Journal of Cancer volume 99, pages 841-846 (16, Sep. 2008); US20030138419; WO2010021822. |
| stress | stress proteins, cytokines, chemokines, apoptotic factors, etc. | receptors, etc. | Milisav (2011). Cellular Stress Responses, Adv. in Regen. Med., S. Wislet-Gendebien (Ed.); WO2006008484. |
| loss of adhesion | cell adhesion molecules (CAMs, e.g., integrins, immunoglobulin (Ig) superfamily, cadherins, and selectins) | CAMs | |
| pathogens | pathogen (bacterial cell, fungus, virus, parasite, etc) or an antigen or toxin therefrom | receptors (e.g., TLRs), antibodies, lectins, fusion proteins | Akira et al. Cell 124, 783-801, Feb. 24, 2006. |
| hypoxia | intracellular oxygen levels | HIFα, HIFβ, heme protein, prolyl hydroxylase | Zhu and Bunn, Science. 2001 Apr. 20; 292(5516): 449-451. |
| heat/temperature | heat | vanilloid receptor; thermosensing transient receptor potential subfamily (thermoTRP) | U.S. Pat. 7,396,910; Moqrich et al., Science 4, Mar. 2005: Vol. 307, Issue 5714, pp. 1468-1472 |

*Each reference is incorporated herein by reference in its entirety for all of its disclosure, including without limitation, all criteria, materials, compounds, compositions, molecules, proteins, components, methods of use and making.

In an aspect, provided herein are methods for making a recombinant cell. The methods include obtaining, in silico, a pathway map of an endogenous pathway in a cell of interest, determining, in silico, a predicted effect of incorporating a recombinant nucleic acid into the endogenous pathway; and based on the predicted effect, incorporating the recombinant nucleic acid into the endogenous pathway in the cell of interest such that activation of the endogenous pathway regulates expression of the recombinant nucleic acid, thereby making a recombinant cell.

In embodiments, the recombinant cell is a recombinant therapeutic cell and the recombinant nucleic acid encodes a therapeutic molecule. Examples of a therapeutic molecule include, but are not limited to, a pro-apoptotic protein, a therapeutic antibody, a chimeric antigen receptor, a secreted or membrane bound protein that binds a signaling molecule (e.g., cytokine, chemokine, etc.), an antisense RNA, an immune stimulating cytokine, a chemokine, a cytotoxic protein, an immune-stimulating protein, a suicide gene, and a sodium iodide symporter (NIS). In embodiments, the therapeutic molecule is a pro-apoptotic protein. In embodiments, the therapeutic molecule is a therapeutic antibody. In embodiments, the therapeutic molecule is a chimeric antigen receptor. In embodiments, the therapeutic molecule is an antisense RNA. In embodiments, the therapeutic molecule is an immune stimulating cytokine. In embodiments, the therapeutic molecule is a chemokine. In embodiments, the therapeutic molecule is a cytotoxic protein. In embodiments, the therapeutic molecule is an immune-stimulating protein. In embodiments, the therapeutic molecule is a suicide gene. In embodiments, the therapeutic molecule is a sodium iodide symporter (NIS). While in some embodiments the recombinant nucleic acid will encode a single recombinant protein (e.g., single pathway element) it should be noted that the recombinant nucleic acid may also encode multiple pathway elements (which may be regulatory elements (e.g., transcription factors, repressors, etc.), intermediate effectors (e.g., kinases, phosphatases, etc.), intracellular, transmembrane, and/or secreted proteins. Likewise, recombinant nucleic acids may also include regulatory elements that are responsive to one or more regulatory proteins or nucleic acids native to the recombinant cell.

In embodiments, the recombinant cell is a bacteria, virus, fungus, yeast, parasite, tumor cell, plant cell, stem cell, or an immune cell. In some embodiments, the immune cell is an immunocompetent cell. In some embodiments, the immune cell is a B cell, dendritic cell, natural killer cell (e.g., an NK92 cells, aNK cells, haNK cell, etc.), an invariant natural killer T cell (iNKT), a T cell, or a CAR-T cell.

In embodiments, the recombinant cell is a recombinant sensor cell and the recombinant nucleic acid encodes a sensor molecule that senses a molecule of interest.

In embodiments, the sensor molecule senses cell density, pH, hypoxia, radio signal, MRI, heat, presence of a molecule of interest, or concentration of a molecule of interest. In embodiments, the sensor molecule senses cell density. In embodiments, the sensor molecule senses pH. In embodiments, the sensor molecule senses hypoxia. In embodiments, the sensor molecule senses radio signal. In embodiments, the sensor molecule senses magnetic resonance imaging (MRI). In embodiments, the sensor molecule senses heat. In embodiments, the sensor molecule senses presence of a molecule of interest. In embodiments, the sensor molecule senses concentration of a molecule of interest.

In embodiments, the molecule of interest is a cytokine, a chemokine, a metabolite, an exosome, an enzyme, a sugar, an intracellular component, a soluble checkpoint inhibitor, a signaling factor, a virus, a yeast cell, or a bacterial cell. In embodiments, the molecule of interest is a cytokine. In embodiments, the molecule of interest is a chemokine. In embodiments, the molecule of interest is a metabolite. In embodiments, the molecule of interest is an exosome. In embodiments, the molecule of interest is an enzyme. In embodiments, the molecule of interest is a sugar. In embodiments, the molecule of interest is an intracellular component. In embodiments, the molecule of interest is a soluble checkpoint inhibitor. In embodiments, the molecule of interest is a signaling factor. In embodiments, the molecule of interest is a virus. In embodiments, the molecule of interest is a yeast cell. In embodiments, the molecule of interest is a bacterial cell.

In embodiments, the recombinant nucleic acid includes a promoter. In embodiments, the promoter is activated by activation of the pathway. In embodiments, the promoter is repressed by activation of the pathway.

In embodiments, the recombinant nucleic acid is incorporated into the cell of interest if the predicted effect would not impact one or more additional endogenous pathways in the cell. In embodiments, the recombinant nucleic acid is incorporated into the cell of interest if the predicted effect would have a minimal impact on one or more additional endogenous pathways in the cell. In embodiments, a minimal impact is one that results in less than 30%, less than 25%, less than 20%, less than 15%, less than 10%, less than 5%, or less than 1% reduction in pathway function. In embodiments, the recombinant nucleic acid is incorporated into the cell of interest if the predicted effect would have a significant impact on one or more additional endogenous pathways in the cell. In embodiments, a significant impact is one that results in greater than 1%, greater than 5%, greater than 10%, greater than 15%, greater than 20%, greater than 25%, greater than 30%, greater than 35%, or greater than 40% increase in pathway function.

In embodiments, the recombinant nucleic acid is incorporated into the cell of interest if the predicted effect would result in higher expression of the recombinant nucleic acid compared to incorporation into a different pathway. In embodiments, a higher expression is one that results in greater than 1%, greater than 5%, greater than 10%, greater than 15%, greater than 20%, greater than 25%, greater than 30%, greater than 35%, or greater than 40% increase in expression compared to incorporation into a different pathway. In embodiments, the recombinant nucleic acid is incorporated into the cell of interest if the predicted effect would result in lower expression of the recombinant nucleic acid compared to incorporation into a different pathway. In embodiments, lower expression is one that results in less than 30%, less than 25%, less than 20%, less than 15%, less than 10%, less than 5%, or less than 1% expression compared to incorporation into a different pathway.

In further embodiments, the recombinant nucleic acid is incorporated into the cell of interest to produce a predicted effect that is not native to the cell without the recombinant nucleic acid. Thus, and viewed from a different perspective, it should be appreciated that entire pathway branches or even pathways can be grafted into a cell to impart a functionality to a particular cell that the cell would otherwise (natively) not possess. Regardless of the desired effect, it is contemplated that some recombinant nucleic acids will encode at least two, or at least three, or at least four pathway elements, wherein at least one of the recombinant pathway elements provides a signal to at least another one of the recombinant pathway elements.

In an aspect, provided herein are methods for making a recombinant cell. The methods include obtaining a pathway map of a first endogenous pathway and a second endogenous pathway in a cell of interest, determining a predicted first degree of impact on the first endogenous pathway of incorporating a first recombinant nucleic acid into the first endogenous pathway, and determining a predicted second degree of impact on the second endogenous pathway of incorporating a second recombinant nucleic acid into the second endogenous pathway. The methods include incorporating the first recombinant nucleic acid into the first endogenous pathway in the cell of interest, if the first degree of impact is of a first desired magnitude, such that activation of the first endogenous pathway regulates expression of the first recombinant nucleic acid; and/or if the second degree of impact is of a second desired magnitude, incorporating the second recombinant nucleic acid into the second endogenous pathway in the cell of interest such that activation of the second endogenous pathway regulates expression of the second recombinant nucleic acid, thereby making a recombinant cell.

In embodiments, the first desired magnitude and/or the second desired magnitude comprises a reduction in activity of the pathway.

In embodiments, the first and/or second desired magnitude is a predicted reduction in the activity of the pathway of at least 10%. In embodiments, the activity of the pathway is predicted to be reduced by at least 20%. In embodiments, the activity of the pathway is predicted to be reduced by at least 30%. In embodiments, the activity of the pathway is predicted to be reduced by at least 40%. In embodiments, the activity of the pathway is predicted to be reduced by at least 50% In embodiments, the activity of the pathway is predicted to be reduced by at least 60%. In embodiments, the activity of the pathway is predicted to be reduced by at least 70%. In embodiments, the activity of the pathway is predicted to be reduced by at least 80%. In embodiments, the activity of the pathway is predicted to be reduced by at least 90%.

In embodiments, the first desired magnitude and/or the second desired magnitude comprises an increase in activity of the pathway.

In embodiments, the first and/or second desired magnitude is a predicted increase in the activity of the pathway of at least 10%. In embodiments, the activity of the pathway is predicted to be increased by at least 20%. In embodiments, the activity of the pathway is predicted to be increased by at least 30%. In embodiments, the activity of the pathway is predicted to be increased by at least 40%. In embodiments, the activity of the pathway is predicted to be increased by at least 50%. In embodiments, the activity of the pathway is predicted to be increased by at least 60%. In embodiments, the activity of the pathway is predicted to be increased by at least 70%. In embodiments, the activity of the pathway is predicted to be increased by at least 80%. In embodiments, the activity of the pathway is predicted to be increased by at least 90%.

In embodiments, the first desired magnitude and/or the second desired magnitude comprises no change in activity of the pathway.

In embodiments, the activity of the pathway is predicted to change by less than 10%. In embodiments, the activity of the pathway is predicted to change by less than 9%. In embodiments, the activity of the pathway is predicted to change by less than 8%. In embodiments, the activity of the pathway is predicted to change by less than 7%. In embodiments, the activity of the pathway is predicted to change by less than 6%. In embodiments, the activity of the pathway is predicted to change by less than 5%. In embodiments, the activity of the pathway is predicted to change by less than 4%. In embodiments, the activity of the pathway is predicted to change by less than 3%. In embodiments, the activity of the pathway is predicted to change by less than 2%. In embodiments, the activity of the pathway is predicted to change by less than 1%.

Provided herein are recombinant cells made by the methods disclosed herein.

Provided herein are methods of treating a patient in need thereof, the method including administering to the patient a therapeutically effective amount of the recombinant cell as described herein.

In an aspect, provided herein are systems including at least one data processor; and at least one memory storing instructions, which when executed by the at least one data processor, result in operations. The operations include creating a hybrid pathway model by at least connecting an endogenous pathway model for a cell coupled to an exogenous pathway model of the cell, the endogenous pathway model having at least one modeled activity, the exogenous pathway model comprising at least one factor for coupling the endogenous pathway model, and the endogenous pathway model and the exogenous pathway model being connected based on the at least one factor; and calculating, based at least on the hybrid pathway model, an activity in the exogenous pathway.

In an aspect, provided herein are methods including creating, by at least one data processor, a hybrid pathway model by at least connecting an endogenous pathway model with an exogenous pathway model, the endogenous pathway model having at least one modeled activity, the exogenous pathway model comprising at least one factor for coupling the endogenous pathway model, and the endogenous pathway model and the exogenous pathway model being connected based on the at least one factor; and calculating, based at least on the hybrid pathway model, a hybrid pathway activity.

In embodiments, the activity at least in the exogenous pathway connects to a measurable output or a physiological signal that affects an endogenous pathway of the same cell or a separate cell.

In embodiments, the hybrid pathway model comprises at least one factor graph. In embodiments, the hybrid pathway model is a social network algorithm applied to pathway analysis.

In embodiments, the hybrid pathway activity includes an increase in exogenous pathway activity, a decrease in exogenous pathway activity, an increase in endogenous pathway activity, and/or a decrease in endogenous pathway activity. In embodiments, the hybrid pathway activity includes in exogenous pathway activity. In embodiments, the hybrid pathway activity includes a decrease in exogenous pathway activity. In embodiments, the hybrid pathway activity includes an increase in endogenous pathway activity. In embodiments, the hybrid pathway activity includes a decrease in endogenous pathway activity.

In embodiments, the system or method further includes generating a pathway activity map across one or more known pathways in at least the endogenous pathway model.

In embodiments, the hybrid pathway activity indicates that one or more endogenous pathways and/or exogenous pathways are orthogonal indicating that one or the other pathway do not significantly impact the other. In embodiments, the hybrid pathway activity indicates that one or more endogenous pathways and/or exogenous pathways are enhanced. In embodiments, the hybrid pathway activity indicates that one or more endogenous pathways and/or exogenous pathways are suppressed. It should be appreciated that such indications (e.g., orthogonal indication, enhanced indication, etc.) illustrate how the exogenous and endogenous pathways interact with each other. Thus, the indications provide in silico evidence that the exogenous pathway might be desirable for use as a compunomic element in a recombinant cell.

In embodiments, the system or method further includes generating, based at least on the hybrid pathway activity, a recommendation to render non-functional at least part of the endogenous pathway.

In an aspect, provided herein are non-transitory computer readable medium storing instructions, which when executed by at least one data processor, result in operations. The operations include creating a hybrid pathway model by at least connecting an endogenous pathway model with an exogenous pathway model, the endogenous pathway model having at least one modeled activity, the exogenous pathway model comprising at least one factor for coupling the endogenous pathway model, and the endogenous pathway model and the exogenous pathway model being connected based on the at least one factor; and calculating, based at least on the hybrid pathway model, a hybrid pathway activity.

Methods of Use

Methods for making a recombinant cell as described herein may be utilized to make a recombinant production reporter cell engineered for quality control protocols for a biological production system, e.g. production of a biological therapeutic. For example, the methods may be used to obtain, in silico, a pathway map of an endogenous pathway in a cell of interest such as an immune cell. The method includes determining, in silico, a predicted effect of incorporating a recombinant nucleic acid, for example, a therapeutic antibody, into the endogenous pathway. Then, based on the predicted effect, the method includes incorporating the recombinant nucleic acid into the endogenous pathway in the cell of interest such that activation of the endogenous pathway regulates expression of the recombinant nucleic acid, thereby making a recombinant cell.

By way of another non-limiting example, the methods described herein may be utilized to make a recombinant cell wherein two recombinant nucleic acids are engineered into two different and separate endogenous pathways such that each endogenous pathway is selected based on the predicted impact on that pathway, predicted by in silico analysis. Incorporation of the nucleic acids into the endogenous pathways occurs if the first degree of impact is of a first desired magnitude, such that activation of the first endogenous pathway regulates expression of the first recombinant nucleic acid; and/or if the second degree of impact is of a second desired magnitude, incorporating the second recombinant nucleic acid into the second endogenous pathway in the cell of interest such that activation of the second endogenous pathway regulates expression of the second recombinant nucleic acid.

By way of another non-limiting example, the methods described herein may be utilized to make a genetically modified therapeutic cell by evaluating the impact of the genetic modification on one or more endogenous pathways in the cell, predicted by in silico analysis. Incorporation of the genetic modification occurs if the impact on the endogenous pathway(s) is within a desired magnitude, for example if the activity of the endogenous pathway is not changed by more than 10% (increase and/or decrease from the activity of an unmodified cell). In some embodiments, it may be desirable to increase or decrease activity of the pathway(s), for example by more than 20%, 30%, 40%, 50%, etc. The cell may be genetically modified by insertion of a therapeutic molecule. By way of example only, the therapeutic molecule may be inserted into an endogenous pathway, such that the expression of the therapeutic molecule is regulated by that pathway.

In one example, a genetically modified T cell that expresses a chimeric antigen receptor (CAR) may be created. In silico analysis as described herein is used to determine whether insertion of the CAR into an endogenous signaling pathway, for example a pathway that is activated by exposure of the cell to a tumor cell microenvironment (change in pH, presence of one or more tumor-specific antigens, etc.), will have a desired (or deleterious) effect on the endogenous pathway.

By way of another non-limiting example, the methods described herein may be utilized to make a genetically modified, conditional therapeutic cell that is responsive to one or more cellular microenvironments. For example, the genetically modified, conditional therapeutic cell may be responsive to a hypoxic microenvironment, such that expression of a therapeutic molecule by the cell is induced under hypoxic conditions. The therapeutic molecule is an exogenous gene, which may be inserted into an endogenous pathway, for example a hypoxia pathway that is activated by exposure of the cell to tumor cell microenvironment hypoxia. The methods described herein may be used to evaluate the impact of inserting the genetic modification at various places within the endogenous hypoxia pathways in the cell, as predicted by in silico analysis. In embodiments, the effect of insertion of the genetic modification is measured by expression (predicted expression) of HIF1 (hypoxia-inducible factor-1), a factor that is upregulated under hypoxic conditions. A factor graph representing the HIF1 pathway can be determined by an in silico model as described herein. The in silico model may be generated using data from any relevant source. The elements of the HIF1 pathway can be incorporated into an existing model probabilistic pathway model such as used by PARADIGM or can be incorporated de novo. One should appreciate that the HIF1 factor graph can be interconnected with other factor graphs based on known interaction points as determined by existing knowledge (e.g., curated genomic articles, known pathways, etc.). Upon executing analysis of the resulting pathway model, the system will generate an indication of the impact on the desired HIF1 pathway, and/or the impact of perturbing the HIF1 pathway on other pathways of interest. If the results are desirable, then the HIF1 pathway (e.g., recombinant gene, etc.) might be a candidate for use in a recombinant cell exhibiting compunomic capabilities.

The methods described herein can be used to predict complex interactions between multiple pathways in a cell of interest. For example, it may be desirable to utilize two or more pathways as a "logic gate," such that certain conditions must be met in order to turn on (or off) expression of a recombinant gene. Any type of logic gate that is turned on or off by at least two conditions is contemplated herein, such as and without limitation, AND, NAND, OR, NOR, XOR, XNOR gates or combination of logical gates that produce more complex functions (e.g., adders, counters, multiplexers, etc.). See, e.g., Weinberg et al, *Nature Biotechnology* 35, pages 453-462 (2017), and U.S. Patent Pub. No. 2017/0183654, each of which is incorporated herein by reference in its entirety. The in silico model as described herein can be used to determine whether insertion of two or more genes into different pathways (such as those indicated in Table 1) is predicted to have a deleterious, advantageous, or neutral effect on various pathways of interest within the cell. The in silico model can be used to determine which candidate pathway(s) would be most (or least) likely to have the desired effect on various pathways of interest within the cell.

For example, and without limitation, the in silico model can be used to identify target pathways for gene insertion in a recombinant therapeutic cell. To engineer a cell that senses both IL-8 and hypoxia in the cellular microenvironment, and expresses a therapeutic molecule only when both conditions are present (i.e., an AND gate), the cell can be engineered to express a gene that senses IL-8 in the microenvironment (e.g., an IL-8 receptor, e.g., CXCR1 or CXCR2) and a gene that senses hypoxia in the cellular microenvironment (e.g., hypoxia inducible factor alpha, HIF1a), along with a recombinant nucleic acid sequence comprising a promoter that is activated only when activated HIF1a and a down-stream effector of the IL-8 receptor (e.g., a transcription factor activated by the IL-8 pathway) are present in the cell. In silico analysis using a model (system) as described herein can be used to determine whether addition of IL-8 receptor and/or HIF1a is predicted to have a deleterious effect on the endogenous cellular pathways, and/or whether the therapeutic gene is predicted to be expressed under the desired conditions, and not expressed under other conditions (for example, in a non-cancerous tissue, e.g., muscle, that may be hypoxic but does not express or over-express IL-8).

In addition or in contrast, in silico analysis as described herein can be used to determine whether inserting the genetic modification into an endogenous signaling pathway will result in the desired expression of the therapeutic molecule (e.g., sufficient expression, properly regulated expression, and the like).

The present disclosure also relates, in part, to methods of making recombinant therapeutic cells as described herein. Methods of genetically modifying cells are well known in the art. See, e.g., M. R. Green and J. Sambrook, Molecular Cloning: A Laboratory Manual (Fourth Edition), Cold Spring Harbor Laboratory Press; (Jun. 15, 2012).

In some embodiments, the nucleic acids are transiently transfected into the cell. In some embodiments, the nucleic acids are stably transfected into the cell. In some embodiments, the nucleic acids are stably transfected into the cell. In embodiments, the nucleic acids are introduced into the cell as a plasmid. In embodiments, the nucleic acids are introduced into the cell as an artificial chromosome. In embodiments, the nucleic acids are introduced into the cell using a viral vector. In embodiments, the nucleic acids are inserted into the cell by homologous recombination, e.g., into a chromosome of the cell. In embodiments, the nucleic acids are inserted into the cell by non-homologous end joining.

In some embodiments, the nucleic acids are inserted into the cell, e.g., the genome of a cell, using a gene editing reagent. Gene editing reagents include, without limitation, RNA-guided nuclease (e.g., CRISPR system, CRISPR/Cas9, CRISPR/cpf1, etc.); meganuclease, zinc finger nuclease (ZFN), or transcription activator-like effector-based nuclease (TALEN).

In embodiments, the methods described herein can be used to make recombinant/genetically modified reporting and/or therapeutic cells as described, for example, in U.S. Application Nos. 62/819,117 and 62/819,113, each of which is incorporated herein by reference in its entirety. In embodiments, the methods described herein can be used to make recombinant/genetically modified sensor cells as described, for example, in U.S. Application No. 62/730,981, incorporated herein by reference in its entirety.

What is claimed is:

1. A method for making a recombinant cell, the method comprising:
   (i) generating, in silico via PARADIGM, a pathway map of an endogenous IL-8 signaling pathway and a HIF-1a signaling pathway in a cell of interest;
   (ii) determining, in silico, an expected effect of incorporating a recombinant nucleic acid on pathways of interest within the cell, wherein the recombinant nucleic acid comprises a promotor that is activated upon sensing IL-8 and HIF-1a signaling, and wherein the promotor controls expression of a sequence encoding a therapeutic molecule; and
   (iii) transfecting the cell of interest with the recombinant nucleic acid, thereby making a recombinant cell that expresses the therapeutic molecule only upon IL-8 and HIF-1a signaling.

2. The method of claim 1, wherein the recombinant cell is a recombinant therapeutic cell.

3. The method of claim 1, wherein the therapeutic molecule is selected from the group consisting of a pro-apoptotic protein, a therapeutic antibody, a chimeric antigen receptor, an antisense RNA, an immune stimulating cytokine, a chemokine, a cytotoxic protein, an immunostimulating protein, a suicide gene, and a sodium iodide symporter (NIS).

4. The method of claim 1, wherein the recombinant cell is a recombinant sensor cell and the recombinant nucleic acid encodes a sensor molecule that senses a molecule of interest.

5. The method of claim 4, wherein the sensor molecule senses cell density, pH, hypoxia, radio signal, MRI, heat, presence of a molecule of interest, or concentration of a molecule of interest.

6. The method of claim 4, wherein the molecule of interest is a cytokine, a chemokine, a metabolite, an exosome, an enzyme, a sugar, an intracellular component, a soluble checkpoint inhibitor, a signaling factor, a virus, a yeast cell, or a bacterial cell.

7. The method of claim 1, wherein the recombinant nucleic acid is incorporated into the cell of interest if the expected effect would not impact one or more additional endogenous pathways in the cell.

8. The method of claim 1, wherein the recombinant nucleic acid is incorporated into the cell of interest if the expected effect would have a large impact on one or more additional endogenous pathways in the cell.

* * * * *